United States Patent [19]

Tennant

[11] 4,242,762
[45] Jan. 6, 1981

[54] POSTERIOR ENCAPSULED IMPLANT LENS

[76] Inventor: J. rald L. Tennant, 806 Greentree Ct., Duncanville, Tex. 75116

[21] Appl. No.: 60,595

[22] Filed: Jul. 25, 1979

[51] Int. Cl.³ .............................. A61F 1/16; A61F 1/24
[52] U.S. Cl. ........................................................... 3/13
[58] Field of Search .......................................... 3/13, 1

[56] References Cited

U.S. PATENT DOCUMENTS

| | | | |
|---|---|---|---|
| 3,673,616 | 7/1972 | Fedorov et al. | 3/13 |
| 3,711,870 | 1/1973 | Deitrick | 3/13 |
| 3,866,249 | 2/1975 | Flom | 3/13 |
| 3,906,551 | 9/1975 | Otter | 3/13 |
| 3,913,148 | 10/1975 | Potthast | 3/13 |
| 3,922,728 | 12/1975 | Krasnov | 3/13 |
| 3,925,825 | 12/1975 | Richards et al. | 3/13 |
| 3,971,073 | 7/1976 | Richards et al. | 3/13 |
| 3,986,214 | 10/1976 | Krasnov | 3/13 |
| 3,991,426 | 11/1976 | Flom et al. | 3/13 |
| 4,010,496 | 3/1977 | Neefe | 3/13 |
| 4,085,467 | 4/1978 | Rainin et al. | 3/13 |
| 4,087,866 | 5/1978 | Choyce et al. | 3/13 |
| 4,092,743 | 6/1978 | Kelman | 3/13 |
| 4,124,905 | 11/1978 | Clark | 3/13 |
| 4,127,903 | 12/1978 | Schachar | 3/13 |

FOREIGN PATENT DOCUMENTS

| | | | |
|---|---|---|---|
| 959314 | 3/1957 | Fed. Rep. of Germany | 3/13 |
| 1034325 | 7/1958 | Fed. Rep. of Germany | 3/13 |
| 1103399 | 5/1955 | France | 3/13 |

OTHER PUBLICATIONS

"The Intraocular Implant Lens Development and Results", published by the Williams & Wilkins Co., Baltimore, Md., 1975, pp. 16-23.

*Primary Examiner*—Ronald L. Frinks
*Attorney, Agent, or Firm*—Richards, Harris & Medlock

[57] ABSTRACT

An artificial intraocular lens (10) for encapsulation in the posterior chamber of an eye includes a generally triangular base element (12) with an optic element (14) positioned therein and a pin (22) extending outwardly from one corner thereof. Following extraction of the natural lens, the artificial lens (10) is positioned in the capsular sac with the optic element (14) posterior to the pupil and secured in place by a combination of tissue scarring within the capsular sac and superior clipping of the lens (10) to the iris with the pin (22). Another embodiment (30) includes an optic element (34) mounted in a support element (32) having two pins (42) extending outwardly from the corners thereof.

15 Claims, 6 Drawing Figures

U.S. Patent  Jan. 6, 1981  4,242,762

POSTERIOR ENCAPSULED IMPLANT LENS

TECHNICAL FIELD

The present invention relates in general to ophthalmology and artificial lens systems. More particularly, this invention concerns an artificial intraocular lens adapted for encapsulation in the posterior chamber of an eye.

BACKGROUND ART

The eye contains a natural crystalline lens which is supported by a capsular bag or sac located behind the pupil and iris. Light is received through the cornea and pupil, and focused by the lens in a sharp image on the retina to provide vision.

Loss of vision can result when the natural lens becomes clouded or opaque, a condition known as a cataract. To prevent blindness, the accepted medical procedure calls for surgical removal of the natural lens from the eyeball followed by adaptation of an artificial lens to correct vision. Absence of the natural lens from the eye is known as aphakia. The optical correction of this condition is called aphakia correction.

There are several approaches to vision restoration or correction. One method entails fitting the patient with glasses. However, glasses reduce peripheral vision, magnify the objects viewed, and are feasible only when cataracts are removed from both eyes because double vision results if glasses are used after cataract removal from a single eye. Glasses, however, are not generally suitable for treatment of cataracts due to the extent of correction required and distortion resulting therefrom.

In another method, a contact lens is worn on the eye to achieve better peripheral vision at a lower magnification factor than glasses. Unfortunately, many cataract patients are relatively advanced in age and have difficulty in adjusting to contact lenses and in manipulating them for insertion, and therefore cannot wear contact lenses.

Yet another more recently developed method of vision correction involves the implantation of an artificial lens within the eye. This is accomplished by a delicate and precise surgical procedure, and there have been various approaches to such devices. Intraocular lens devices, of course, must be accurately designed and implanted for successfully restoring vision while minimizing irritation of sensitive eye structure and postoperative complications. It will be apparent that minute changes in the design and implantation technique of such lenses can be determinative of success or failure.

Intraocular lenses have been developed for placement in the anterior chamber as well as in the posterior chamber. After unsuccessful attempts by Harold Ridley and others to develop lenses for placement in the posterior chamber, efforts turned to development of anterior chamber devices. Fixation and centration, however, are problems common to both types of lenses.

Intraocular lenses must be implanted and stabilized in a way which is resistant to dislocation, but which accommodates the involuntarily movement of the iris. In order to minimize these problems, several types of iris-clip and iridocapsular lenses have come about. For example, a lens known as the Binkhorst iris-clip lens uses nylon loops which are sutured to the iris. Suturing is undesirable because special techniques are required in their installation, in addition to the fact that sutures may tear loose from the iris and eventually dissolve to cause dislocation of the lens. Other intraocular lens designs employ one or more loops in combination with one or more pins to attach the lens to the iris. Single pin lenses of the prior art, however, have tended to become dislocated in some cases.

Although anterior chamber lenses have been more popular, there are cases in which posterior chamber lenses are preferred by some surgeons. For example, a posterior chamber lens may be preferable in cases of traumatic cataract requiring extracapsular extraction of the natural lens. However, the lack of a scleral spur in the posterior chamber, which is the natural location, poses a special problem in that the lens must be placed in the more sensitive ciliary body.

Difficulties with previous posterior chamber lenses included nonfixation, poor centration and other complications. One prior design effects centration by the spring action of opposed resilient legs engaged with the ciliary body, the long term effect of which is unknown but potentially detrimental. In another posterior chamber design of the prior art, centration is effected by a suture between the upper haptic thereof and the iris. Dilation of the pupil can cause dislocation of this lens design. Another design employs a plurality of prongs or pins clipped to the iris about the pupil.

There is thus a need for an improved intraocular lens for encapsulation in the posterior chamber which allows movement of the iris relative thereto with increased stability against dislocation and thus decentration of the lens.

DISCLOSURE OF THE INVENTION

The present invention comprises an intraocular lens which overcomes the foregoing and other difficulties associated with the prior art. In accordance with the invention, there is provided an intraocular implant adapted for insertion in the posterior chamber behind the iris. The lens utilizes at least one flexible pin for clipping to the iris, together with capsular fixation to achieve greater stability and resistance against movement to maintain centration.

In accordance with more specific aspects of the invention, there is provided an artificial lens for implantation in the posterior capsule of the eye after extraction of the natural lens therefrom. In one embodiment, the lens comprises a generally triangular haptic support with a single pin extending outwardly therefrom and an optic element mounted therein. Another embodiment of the invention comprises a generally rectangular haptic support with two pins extending outwardly therefrom and an optic element mounted therein. The lens element is clipped to the iris by the pin or pins at one end thereof, and secured at the other end thereof by capsular fixation. The configuration and attachment of the intraocular lens herein results in better stability and increased resistance against dislocation by reason of clip suspension and capular support in combination.

BRIEF DESCRIPTION OF DRAWINGS

A more complete understanding of the invention can be had by reference to the following Detailed Description in conjunction with the accompanying Drawings, wherein.

DETAILED DESCRIPTION

Figure 1:
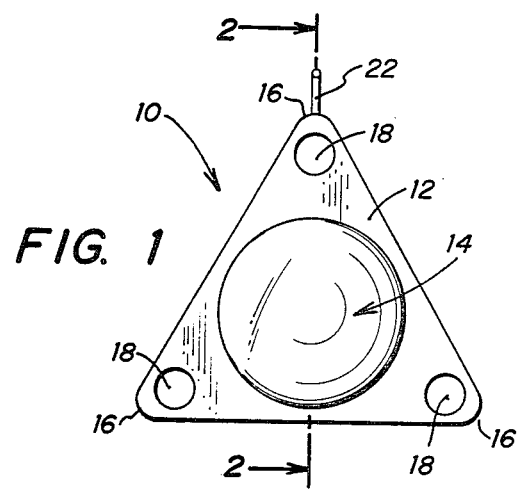
FIG. 1 is a front view of an intraocular lens incorporating a first embodiment of the invention.
Figure 2:
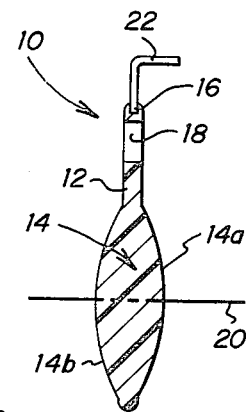
FIG. 2 is a sectional view taken along line 2—2 of FIG. 1 in the direction of the arrows.

Referring now to the Drawings, wherein like reference numerals designate like or corresponding parts throughout the several views, and particularly referring to FIGS. 1 and 2, there is shown an intraocular lens 10 representing a first embodiment of the invention. The lens 10 is useful in restoring vision to a patient following cataract surgery. In particular, intraocular lens 10 is adapted to be implanted in the posterior chamber of the eye following surgical removal of the natural lens therefrom.

Intraocular lens 10 includes a generally triangular base or haptic 12 within which a circular lens element or optic 14 is mounted. Haptic 12 is substantially planar, and is preferably configured in the form of an equilateral triangle having dimensions of about 11 mm per side. The outer edges of haptic 12 are preferably rounded about the margins thereof, as is best shown in FIG. 2. Haptic 12 includes three rounded corners 16 each of which is connected to the other corners by substantially straight sides. A hole 18 is provided in haptic 12 between each rounded corner 16 and optic 14 for weight reduction and to facilitate capsular fixation by scarring.

Haptic 12 is formed of a suitable material which is biologically inert and not susceptible to rejection or absorption of the body. For example, haptic 12 may be formed of polymethylmethacrylate or pHEMA.

The optic 14 of intraocular lens 10 is centrally positioned in haptic 12. Optic 14 may be bi-convex, as illustrated, or plano-convex if desired. The thickness of optic 14 along optical axis 20 varies in accordance with the power of lens 10. Optic 14 is typically five to six millimeters in diameter. Surface 14a comprises the anterior surface of optic 14, while surface 14b comprises the posterior surface thereof.

Haptic 12 and optic 14 are preferably manufactured as an integral unit, whereby the optic would be formed of the same material as the haptic. If desired, however, the optic 14 may be formed of a different material and fused to haptic 12. For example, optic 14 can be formed of pHEMA material with haptic 12 being formed of polymethylmethacrylate material to provide a lens 10 of relatively lighter weight than one constructed entirely of polymethylmethacrylate.

A clip or pin 22 is provided in one of the three corners 16 of haptic 12 in lens 10. Pin 22 extends outwardly from haptic 12 in a direction generally parallel with the plane of the haptic, and terminates in an anteriorly turned portion. Pin 22 is formed of a semi-rigid malleable material which is not subject to rejection or absorption by the body. For example, pin 22 can be formed of platinum or platinum-iridium material. Pin 22 is utilized to clip intraocular lens 10 to the iris of the eye, and is illustrated in FIGS. 1 and 2 in the initial position before insertion of the lens and bending of the pin.

Implantation of intraocular lens 10 goes as follows. Following sedation and preparation of the patient, a small incision is made along the base of the cornea, after which the cornea is carefully lifted up for access to the inner eye. The natural lens of the eye is then removed by extracapsular extraction. The posterior portion of the sac is left intact while an opening is formed in the anterior portion of the sac. Preferably, a triangular opening is formed in the anterior capsule such that one corner of the triangle is oriented in a downward or inferior direction. Lens 10 is then inserted into the posterior chamber between the anterior and posterior portions of the capsule. Pin 22 is inserted from a posterior position through an iridectomy formed in the superior portion of generally twelve o'clock position of the iris, and clipped thereto. The lower or inferior portion of lens 10 is secured by capsular fixation, which scars the lens in place within about four days.

Lens 10 is thus secured in place by the combination of suspension by pin 22 from the iris and tissue scarring within the natural lens capsule. The three-cornered configuration of lens 10 provides increased resistance against rotational and lateral movement of the lens which could cause misalignment thereof relative to the pupil. Closure and suturing of the cornea completes the implantation procedure.

Figure 3:
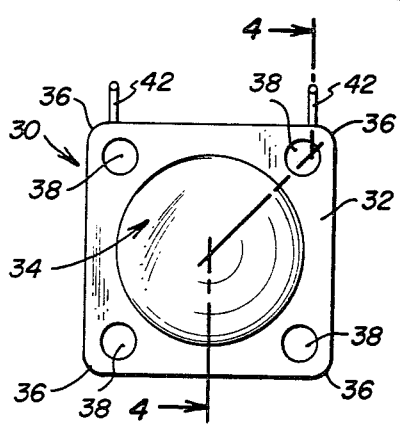
FIG. 3 is a front view of an intraocular lens incorporating a second embodiment of the invention.
Figure 4:
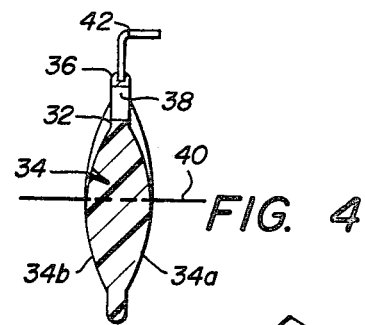
FIG. 4 is a sectional view taken along line 4—4 of FIG. 3 in the direction of the arrows.

FIGS. 3 and 4 illustrate an intraocular lens 30 incorporating a second embodiment of the invention. Lens 30 is constructed of similar materials to lens 10, and is encapuled through a similar procedure. Lens 30 includes a generally rectangular base or haptic 32 and a circular lens element or optic 34, both of which can be formed as an integral unit if desired. Haptic 32 is substantially planar with rounded edges about the margin thereof, as is best shown in FIG. 4, and though shown as a square in configuration is preferably approximately 11 mm by 7 mm dimensionally. Haptic 32 includes four rounded corners 36, each of which extends to two adjacent corners by substantially straight sides. Holes 38 are provided in haptic 32 between corners 36 and optic 34 for weight reduction and to facilitate capsular fixation of lens 30. Haptic 32 can be formed of polymethylmethacrylate, pHEMA or other suitable materials.

Optic 34 is centrally positioned in haptic 32 of lens 30. Optic 34 may be constructed of polymethylmethacrylate, pHEMA or other suitable material. The diameter of optic 34 is about five to six millimeters. The thickness of optic 34 along optical axis 40 varies in accordance with the corrective power required.

Lens 30 further includes a pair of pins 42 extending outwardly in generally parallel relationship from one side of haptic 32. Pins 42 extend from an adjacent pair of corners 36, and each pin includes substantially straight portion extending in generally parallel relationship with the plane of haptic 32 terminating in an anteriorly turned portion. Pins 42 are preferably formed of a semi-rigid malleable material, such as platinum or platinum-iridium.

Lens 30 is clipped by pins 42 through iridectomies formed in the superior portion of the iris in the manner hereinbefore described with regard to lens 10. Lens 30 is secured in place by a combination of clipping to the iris at the superior portion thereof and scarring in place to effect capsular fixation at the lower portion thereof. Lens 30 thus employs a pair of pins 42, whereas lens 10 utilizes a single pin 22 for connection to the iris.

Figure 5:
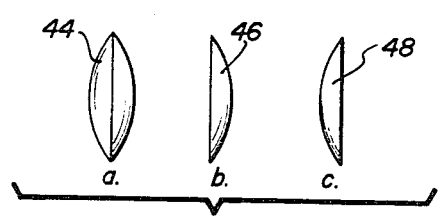
FIGS. 5a, 5b and 5c illustrate optic elements which can be utilized in the invention.

FIG. 5 illustrates three examples of lens elements which can be used in intraocular lenses 10 or 30. FIG. 5a shows a convex-convex or bi-convex lens element 44. A plano-convex lens element 46 is shown in FIG. 5b. FIG. 5c illustrates a convex-plano lens element 48. It will be understood that any of these types of lens elements can be utilized in lenses 10 and 30, as desired.

Figure 6:
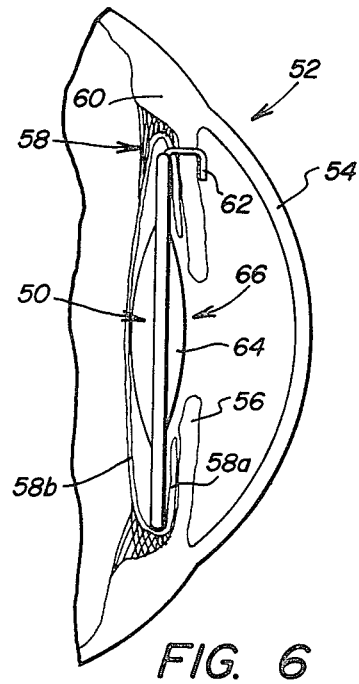
FIG. 6 is a horizontal section through an eyeball, partially broken away, illustrating implantation of the invention.

Referring to FIG. 6, there is shown a cross-sectional view of an intraocular lens 50 of the present invention implanted within an eyeball 52 including a cornea 54 and an iris 56. Lens 50 can be either one of the lenses 10 or 30 hereinbefore described. Lens 50 is positioned in the posterior chamber behind iris 56 and within the lens capsule 58 attached to the ciliary body 60. Lens 60 includes at least one pin 62 which is used to clip the lens to iris 56 at the superior end thereof. In addition to clipping engagement between lens 50 and iris 56, the lens is also fixated by tissue scarring between the anterior and posterior capsule portions 58a and 58b of capsule 58 to maintain centration of optic 62 relative to pupil 64.

From the foregoing, it will be understood that the present invention comprises an improved intraocular lens for posterior chamber encapsulation which has numerous advantages over the prior art. The lens herein utilizes a combination of mechanical iris-clip fixation and capsular fixation by tissue scarring to achieve better stability and attachment of the lens. Other advantages will suggest themselves to those skilled in the art.

Although particular embodiments of the invention have been illustrated in the accompanying drawings and described in the foregoing Detailed Description, it will be understood that the invention is not limited to the embodiments disclosed, but is intended to embrace any alternatives, modifications, and rearrangements and/or substitutions of parts or elements as fall within the spirit and scope of the invention.

I claim:

1. An artificial intraocular lens, comprising:
    a substantially flat base element dimensioned for implantation in the posterior chamber of an eye adjacent to the iris;
    said base element having coplanar posterior and anterior surfaces and a multi-sided periphery with rounded corners;
    an optic element mounted substantially centrally in said base element; and
    pin means extending outwardly from the periphery of at least one corner of said base element for clipping the lens to the iris.

2. The lens of claim 1, wherein the base element is generally triangular and includes three rounded corners.

3. The lens of claim 1, wherein the base element is generally rectangular and includes four rounded corners.

4. The lens of claim 1, wherein the edges of said base element are rounded between the anterior and posterior surfaces about the entire periphery thereof.

5. The lens of claim 1, wherein said base element includes a plurality of holes formed therethrough about said optic element.

6. An artificial intraocular lens for encapsulation in the posterior chamber of an eye to correct vision, which comprises:
    a substantially flat base element dimensioned for insertion in the capsular sac adjacent to the iris in the posterior chamber of the eye;
    said base element having anterior and posterior surfaces and a generally triangular configuration with rounded corners therein;
    an optic element mounted substantially centrally in said base element; and
    pin means extending outwardly from one corner in the periphery of said base element for clipping one end of the lens to the iris, the other end of the lens being secured by tissue scarring within the capsular sac.

7. The lens of claim 6, wherein the periphery of said base element is rounded between the anterior and posterior surfaces about the entire periphery thereof.

8. The lens of claim 6, wherein said base element includes holes formed therethrough between said optic element and the corners of said base element.

9. The lens of claim 6, wherein said pin means comprises:
    a single pin of semi-rigid material with an inner portion extending outwardly substantially within the plane of said base element and an outer portion turned substantially perpendicular to said plane.

10. The lens of claim 6, wherein the base and optic elements are formed as an integral unit.

11. An artificial intraocular lens for encapsulation in the posterior chamber of an eye to correct vision, which comprises:
    a substantially flat base element dimensioned for insertion in the capsular sac adjacent to the iris in the posterior chamber of the eye;
    said base element having anterior and posterior surfaces and a generally rectangular configuration with four rounded corners;
    an optic element mounted substantially centrally in said base element; and
    pin means extending outwardly from two corners in the periphery of said base element for clipping one end of the lens to the iris, the other end of the lens being secured by tissue scarring within the capsular sac.

12. The lens of claim 11, wherein the margin of said base element is rounded between the anterior and posterior surfaces about the entire periphery thereof.

13. The lens of claim 11, wherein said base element includes holes formed therethrough between said optic element and the corners of said base element.

14. The lens of claim 11, wherein each of said pin means comprises:
    a single pin of semi-rigid material with an inner portion extending outwardly substantially within the plane of said base element and an outer portion turned substantially perpendicular to said plane.

15. The lens of claim 11, wherein the base and optic elements are formed as an integral unit.

* * * * *